United States Patent
Katsukura

(12) 
(10) Patent No.: US 6,203,827 B1
(45) Date of Patent: Mar. 20, 2001

(54) COMPOSITION CONTAINING READILY ABSORBABLE CALCIUM AND PROCESS FOR PRODUCING THE SAME

(75) Inventor: Shinya Katsukura, Tokyo (JP)

(73) Assignee: Masahiko Nishimura (JP)

( * ) Notice: Subject to any disclaimer, the term of this patent is extended or adjusted under 35 U.S.C. 154(b) by 0 days.

(21) Appl. No.: 08/952,738

(22) PCT Filed: Apr. 5, 1996

(86) PCT No.: PCT/JP96/00938

§ 371 Date: Nov. 25, 1997

§ 102(e) Date: Nov. 25, 1997

(87) PCT Pub. No.: WO96/38058

PCT Pub. Date: Dec. 5, 1996

(30) Foreign Application Priority Data

May 28, 1995 (JP) ................................................. 7/153987

(51) Int. Cl.⁷ .................................................. A23K 1/175
(52) U.S. Cl. ............................................................. 426/74
(58) Field of Search ............................... 106/260; 420/41, 420/84; 423/555, 554; 424/601, 602, 675, 678, 687, 693, 696; 426/267, 531, 74, 549, 590, 656, 648, 574; 623/11, 16, 66, 77, 901

(56) References Cited

U.S. PATENT DOCUMENTS

| | | | |
|---|---|---|---|
| 4,430,356 | * 2/1984 | Ohyabu et al. | 426/574 |
| 4,786,510 | * 11/1988 | Nakel et al. | 426/74 |
| 5,433,751 | * 7/1995 | Christel et al. | 623/16 |
| 5,620,709 | 4/1997 | Kumagai et al. | 424/682 |

FOREIGN PATENT DOCUMENTS

| | | |
|---|---|---|
| 0 648 495 | 4/1995 | (EP) . |
| 8-103246 | 4/1996 | (JP) . |

* cited by examiner

*Primary Examiner*—Donna Wortman
(74) *Attorney, Agent, or Firm*—Liniak, Berenato, Longacre & White

(57) ABSTRACT

A composition containing readily absorbable calcium which comprises a calcium salt and 0.2 to 5% by weight of chondroitin sulfate based on the calcium content in the calcium salt. A calcium salt preferably used in this composition is obtained by, for example, baking external skeletons of sea urchins in an oven to thereby give calcium oxide, hydrating it into calcium hydroxide and then reacting it with an organic carboxylic acid to thereby give a calcium salt. The absorption of calcium in vivo is highly promoted by adding chondroitin sulfate. As a calcium source various natural and synthetic calcium can be used.

5 Claims, 2 Drawing Sheets

COMPOSITION CONTAINING READILY ABSORBABLE CALCIUM AND PROCESS FOR PRODUCING THE SAME

TECHNICAL FIELD

This invention relates to a composition containing readily absorbable calcium and to a process for producing the same.

BACKGROUND ART

Calcium is one of constituent ingredients of bones and teeth, and it is of importance as a factor regulating muscles, nervous systems and hormone secretion for maintaining functions of a living body. Furthermore it has been proved that it affects immunological functions. Though it is known that lack of calcium ingestion affects development of bone diseases, as well as adult diseases such as hypertension, ischemic heart diseases and endocrine diseases and calcium has been becoming of general interest, the amount thereof ingested in the food life is not yet sufficient in our country. Therefore, various calcium preparations and health foods containing calcium have been proposed and sold on the market for making up the deficiency.

For example, chemically synthesized calcium compounds, calcium compounds originating in shellfishes, crustaceans, eggshells and animals' bones, and calcium originating in plants such as seaweeds have been used so far, but the absorption in vivo of such calcium is not so high and in many cases where they are used as preparations or food additives, they have difficulties in their taste and flavor, so that they have not yet been in popular use.

The present inventor et. al have noted on obtaining calcium having good absorbability in vivo and nice taste and flavor upon ingestion, and capable of providing calcium preparations or food additives containing such calcium from natural animal materials which are stable calcium sources and, as a result of experiment and investigation, have found that calcium compounds obtained by baking external skeletons of sea urchins which are composed of spines and shells can satisfy such purpose, and have further proceeded with the investigation and development of a practical process for producing them, and of the formulation of a composition obtained through the process which contain, calcium compounds originating in sea urchins as a main component.

During such process, the inventor has discovered that the amount of calcium absorbed in vivo is remarkably increased by compounding an appropriate amount of chondroitin sulfate, which belongs to sulfomucopolysaccharides, into the thus obtained calcium compound, the result of which has been filed as Japanese Patent Application Hei 6-260996. As a result of further investigation and development, it has been found that addition of chondroitin sulfate markedly promotes the absorption of calcium in vivo not only in the case of calcium originating in shells of sea urchin but also in the case of calcium originating in other animals or ordinary calcium salts obtained by synthesis such as calcium lactate and calcium carbonate. As described above, absorption of calcium in vivo is promoted by the addition of chondroitin sulfate and it has been also found that the absorption shows specific dependence on the concentration of chondroitin sulfate.

Although the chondroitin sulfate markedly promotes the absorption of calcium in vivo, it is never likely that this increases calcium concentration in blood so rapidly as to break the calcium balance in blood.

DISCLOSURE OF THE INVENTION

The present invention has been accomplished based on the foregoing knowledge of the present inventor, et. al, and the first feature of the present invention resides in a food composition containing readily absorbable calcium, which comprises a calcium salt and 0.2 to 5% by weight of chondroitin sulfate on the basis of a calcium content in the calcium salt described above.

More preferably, the ratio of chondroitin sulfate to the calcium content in the calcium salt is 0.3 to 2.5% by weight.

A more concrete feature of the present invention applied to the use of natural calcium sources resides in a food composition containing readily absorbable calcium, which comprises a calcium salt of an organic carboxylic acid obtained by processing external skeletons of sea urchins and 0.2 to 5% by weight of chondroitin sulfate on the basis of the calcium content in the calcium salt.

A third feature of the present invention resides in a process for producing a food composition containing readily absorbable calcium, wherein the process comprises baking and hydrating external skeletons of sea urchins thereby forming calcium hydroxide, which is then neutralized by reaction with an organic carboxylic acid, thereby forming a calcium salt of the organic carboxylic acid, and adding 0.2 to 5% by weight of chondroitin sulfate on the basis of a calcium content in the calcium salt.

In a food composition of the present invention containing readily absorbable calcium, since it comprises 0.2 to 5% by weight of chondroitin sulfate on the basis of the calcium content in the calcium salt, absorption of calcium in vivo is markedly promoted. Chondroitin sulfate, like heparin, kerato sulfate and hyalurono sulfate, belongs to sulfomucopolysaccharides which exist widely in the animal kingdom and, particularly, chondroitin sulfate and its salt have been already proved for their safety as food additives (emulsion stabilizer, fish odor remover).

Chondroitin sulfate is a water soluble polymer having a molecular weight of about 50,000, in which sulfuric acid is ester-linked to reiteratedly bonded disaccharides comprising a derivative of chondrosamine and D-glucuronic acid coupled in β-glycoside-linkage, an aqueous solution of which is viscous and which is obtained as a C-isomer of chondroitin sulfate, for example, from shark cartilage.

When chondroitin sulfate or the like is blended into a calcium salt, absorption of calcium in vivo is markedly improved as mentioned above. The reason is not completely clear but since sulfomucopolysaccharides are generally liable to combine with protein, it is considered that, upon absorption of calcium into cells through the cell surface of intestinal membranes in the form of Ca-bound protein, chondroitin sulfate interacts with lactic acid or the like which is a constituent acid of a calcium salt, to promote absorption of calcium under the influence of the interaction therewith.

As to the amount of chondroitin sulfate blended into the calcium salt, improvement in the absorption of calcium is recognized even with an extremely small addition amount, for example, of 0.01% by weight of chondroitin sulfate on the basis of the calcium content but, at about 6% by weight, the absorbability is rather lowered markedly. The effect of chondroitin sulfate becomes remarkable from about 0.2% by weight to the calcium content and an especially excellent absorbability is exhibited at 0.3 to 2.5%. On the other hand, in excess of 1%, the above-mentioned effect tends to gradually decrease and, especially, when it is more than 5%, the effect of promoting the absorption of calcium is markedly lowered.

Therefore, in the present invention, about 0.2 to 5% by weight, preferably, 0.3 to 2.5% by weight of chondroitin sulfate is added on the basis of the calcium content.

Considering safety upon ingestion in a living body, calcium is preferably used in the form of an inorganic salt, such as carbonate, and an organic carboxylic acid salt. As a source of calcium, synthesized calcium salts such as calcium lactate, calcium citrate and calcium carbonate can be used, but calcium salts of various carboxylic acids obtained by baking and hydrating natural calcium sources, for example, sea urchin shells, shells and egg shells are preferred. In the present invention, among the above-mentioned natural calcium sources, calcium obtained by baking sea urchin's external skeletons is particularly preferred.

Sea urchins have crystals of calcium carbonate accumulated in the body walls of them, which are combined as calcic plates to form external skeletons. Ovaries of sea urchins are mainly extracted and served for food, while their external skeletons are mostly thrown away as they are, except for being partially used as fertilizers for farming and this causes a problem of fishery wastes. However, sea urchin shells are mostly composed of calcium, and they are a well-balanced calcium source which contain relatively large amount of trace mineral ingredients such as magnesium, potassium, sodium, phosphorus and zinc. In addition, from the viewpoint of industrial use, they are easy to obtain economically as fishery wastes as mentioned above.

Sea urchins used in the present invention belong to the echinodermata, echinoidea, and typical examples of those served for food can include, for example, Hemicentrotus pulcherrimus and Strogylocentrotus intermedius of Storongylocentrotidae, Anthocidaris crassispina of Echinometridae and Tripneustes gratilla of Toxopneustidae, and large quantities of various kinds of sea urchins have been imported recently from overseas such as North America and Korea.

In the present invention, for example, external skeletons of sea urchins, from which ovarian sections have been extracted, are used as raw materials, at first washed with water, and then dried appropriately. Then, they are heated in a usual heat-resistant furnace. In this case, calcium carbonate contained in sea urchin shells is converted into calcium oxide by heating at about 950 to 1150° C., and when heated at that temperature, almost all of the raw materials are converted into calcium oxide in about one hour and baking operation is completed, though this depends on the structure of the furnace.

After cooling, water is added to calcium oxide to produce calcium hydroxide in the form of white powder, which is then neutralized with various kinds of acids into the form of calcium salts which can be safely taken in a body. In this case, unlike calcium carbonate, calcium hydroxide does not give $CO_2$ at the time of neutralization reaction, so that it is very easy to handle in an aqueous solution after reaction. The organic acid is used by a little stoichiometrically excessive amount, relative to the amount of calcium hydroxide such that there should not exist any free calcium hydroxide in the aqueous solution. Although the strict amount varies depending on the kind of the acid and on the application use of the composition obtained, the amount is such that the pH value of the aqueous solution is about 5 to 6 after reaction.

As to the acid used for neutralization, considering safety upon ingestion, solubility, absorption of calcium in vivo, and taste and flavor, organic carboxylic acids generally used in the field of food industry are employed, and L-lactic acid, citric acid, inalic acid, succinic acid, gluconic acid, acetic acid, L-ascorbic acid, etc. are used depending on application uses.

The blend thus obtained, which is in the form of an aqueous solution, is then spray dried into the form of a powder or granule, and it is used in the form of a powdery or tablet-like product depending on application uses, and furthermore in the form of an aqieous solution as a health drink. In order to make the granulation process easier, an excipient such as sugar alcohol and, in particular, that of reducing maltose or erythritol is preferably used. Into the calcium blend in this form, chondroitin sulfate is compounded at a ratio within the foregoing range.

For calcium originating in sea urchin shells which is preferably used in the present invention, since calcium oxide obtained by baking external skeletons of sea urchins is once converted into calcium hydroxide, subsequent treatment such as neutralization reaction becomes easier. Furthermore, since this is converted into the form of calcium salt of the organic acid through neutralization reaction with the foregoing organic carboxylic acid, calcium can be ingested safely and absorbed at a high rate in vivo. Organic acids to be used can be appropriately chosen regarding their type in consideration of the safety and the absorbability as mentioned above and, in addition, of the solubility, etc. depending on application uses.

Calcium originating in sea urchin shells in itself is superior in the absorbability in vivo compared with synthesized calcium carbonate, eggshells' calcium and calcium originating in shells. As mentioned above, sea urchin shells contain calcium as a main component (50% or more), as well as magnesium at a specifically high content (about 2%) and it is generally known for magnesium that it affects the absorption process of calcium in vivo. In addition, trace elements such as sodium, potassium, sulfur, phosphorus, iron and zinc are contained in a well-balanced state, and it is considered that they also contribute to the absorbability of calcium in vivo. For heavy metals such as Hg, CD, PBS and As, they are at about 1 PPM or less, or not detected at all.

BEST MODE FOR CARRYING OUT THE INVENTION

The present invention will be further explained with reference to the following examples.

EXAMPLE 1

Process for Producing Calcium Originating in Sea Urchin Shells

External skeletons of Hemicentrotus pulcherrimus, from which ovaries had been already extracted, were washed with water and dried spontaneously, and then baked in a baking furnace at about 1,100° C. for one hour to give calcium oxide, which was fully hydrated and converted into calcium hydroxide. 1,000 g of thus obtained calcium hydroxide was dissolved in 10 liter of water, about 5,000 g of 50% L-lactic acid was added and reacted at a temperature of 75° C. for 15 min to produce calcium lactate from sea urchin shells. In this case, lactic acid was added in such a little stoichiometrically excessive amount that the pH value of the aqueous solution be at a prescribed value in a range of about 5 to 6 after the reaction, and the reaction process was finished at the time the pH value was settled. To this aqueous solution, 150 g of reducing maltose and about 15 g of chondroitin sulfate composition at 20% purity (ratio of 20% chondroitin sulfate composition to calcium: about 0.5%, ratio of chondroitin sulfate (100%) to calcium: about 0.6%) were added, and dried by a spray-drier to give highly water-soluble particles of 60 μm or less in average diameter which were almost white and had a slightly peculiar taste.

EXAMPLE 2

Fine particles containing calcium were produced in the same procedures as in Example 1 except that chondroitin sulfate was added to an aqueous solution of synthesized calcium carbonate and that of synthesized calcium lactate at the same ratio as in Example 1.

COMPARATIVE EXAMPLE

Compositions containing calcium lactate obtained from sea urchin shells in the product-on process of Example 1, synthesized calcium lactate and synthesized calcium carbonate, respectively, in the same ratio as in Example 1 but not containing chondroitin sulfate were prepared.

Experimental Example 1

Test for Calcium Absorption

Absorption of calcium into rats' intestines was tested using the compositions containing calcium salts which were obtained in each of the above-mentioned examples. For comparison, compositions containing calcium salts in the comparative example were served for the test.

| Calcium Salts served for test | Abbreviations |
| --- | --- |
| Calcium carbonate | $CaCO_3$ |
| Calcium lactate | LaCAL |
| Calcium lactate produced from sea urchin shells | UCAL |
| Calcium lactate + chondroitin | LaCAL* |
| Calcium carbonate + chondroitin | $CaCO_3$* |
| Calcium lactate from sea urchin shells + chondroitin | UCAL* |

Figure 1:
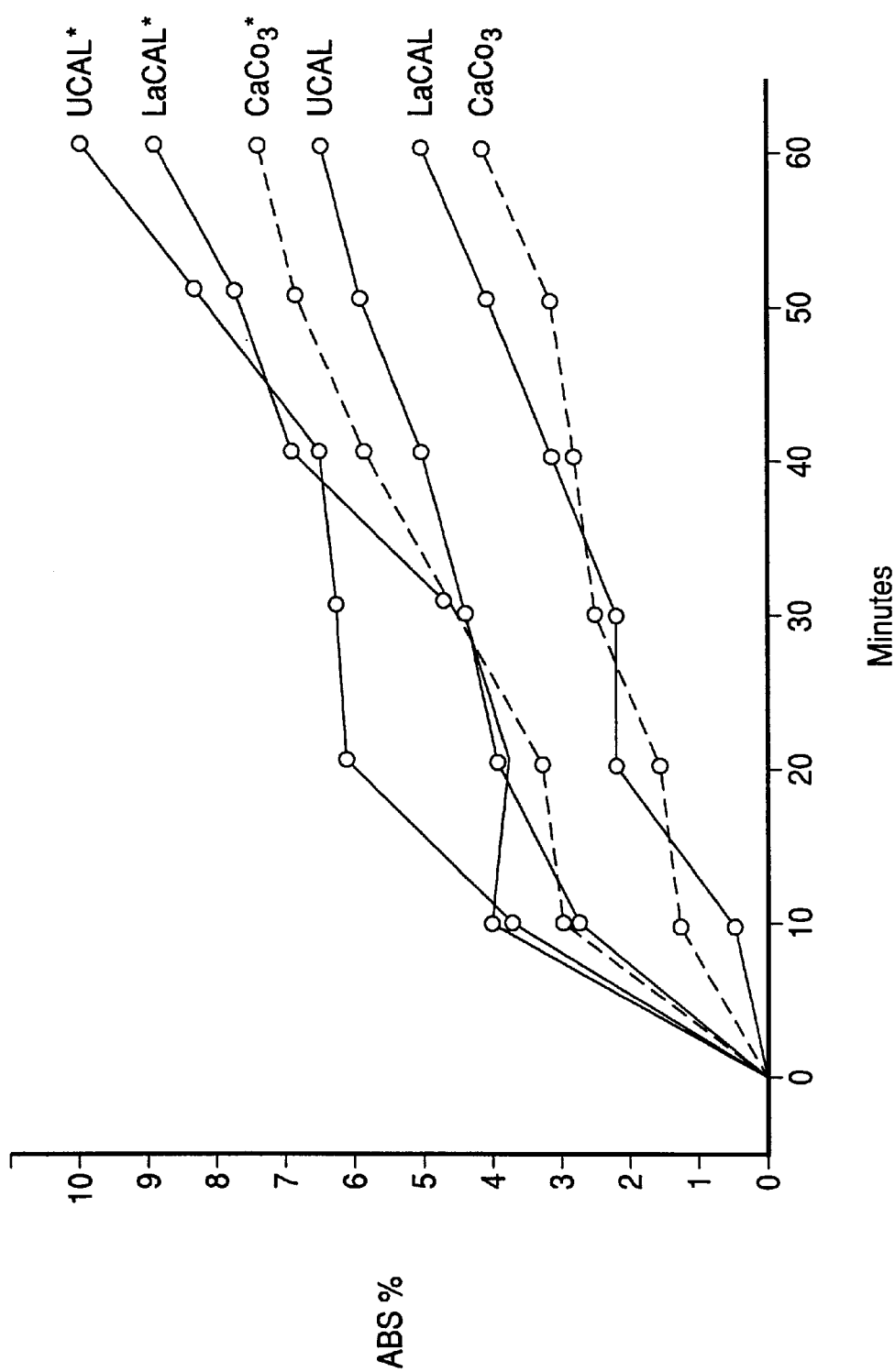
FIG. 1 is a graph which illustrates the absorption of calcium into intestines (Absorption calcium) (%) with circulation time (min), wherein the ratio of chondroitin sulfate is set constant (0.6%) relative to calcium in compositions containing various calcium salts obtained in each of examples of the present invention.

Test Method 100 ml of an artificial intestinal juice at a pH value of 6.5 which contained a composition of each of the above-mentioned calcium salts (12 mg, calculated as calcium) was prepared, circulated in small intestines of rats (Wister: male) of about 8-week old (200 g in weight) through a range from the pyloric region to 6 cm downward as a perfusion zone, from which the effect of the bile juice was removed at 37° C., at a perfusion rate of 1 ml per min to absorb calcium. Five rats mentioned above were used as a group for each of the calcium salts served for the test:, without applying any load promoting the absorption of calcium, such as extraction of parathyroid or administration of vitamin, except for giving no food to the rats for 24 hours. The ratio for the absorption of calcium was determined for each the calcium salts served for test respectively based on the reduction amount of calcium in the circulating solution. The results are shown in Table 1 and FIG. 1. In FIG. 1, the abscissa indicates the passage of the circulation time (min) and the ordinate indicates the ratio of calcium absorbed into intestine, ABS (%), respectively.

TABLE 1

| | Circulating time (min) | | | | | |
| --- | --- | --- | --- | --- | --- | --- |
| | 10 | 20 | 30 | 40 | 50 | 60 |
| UCAL* | 3.78 ± 0.06 | 6.15 ± 0.17 | 6.32 ± 0.10 | 6.56 ± 0.05 | 8.36 ± 0.10 | 10.16 ± 0.20 |
| LaCAL* | 4.05 ± 1.01 | 3.82 ± 0.83 | 4.55 ± 0.23 | 6.96 ± 0.38 | 7.82 ± 0.46 | 9.05 ± 0.53 |
| $CaCO_3$ | 3.06 ± 0.58 | 3.33 ± 0.22 | 4.61 ± 0.31 | 5.90 ± 0.35 | 6.92 ± 0.22 | 7.49 ± 0.23 |
| UCAL | 2.83 ± 0.15 | 3.99 ± 0.11 | 4.47 ± 0.15 | 5.06 ± 0.17 | 6.01 ± 0.30 | 6.58 ± 0.17 |
| LaCAL | 0.47 ± 0.66 | 2.32 ± 0.66 | 2.32 ± 0.66 | 3.25 ± 0.69 | 4.19 ± 0.03 | 5.12 ± 0.67 |
| $CaCO_3$ | 1.32 ± 0.47 | 1.65 ± 0.47 | 2.64 ± 0.48 | 2.97 ± 0.82 | 3.29 ± 0.47 | 4.28 ± 0.48 |

As shown in Table 1 and FIG. 1, the absorption ratio of calcium in 60-minute perfusion is apparently higher in the compositions of Examples 1 and 2, with addition of the chondroitin sulfate, than in the compositions of comparative examples, with no addition of chondroitin sulfate, which indicates excellent effect by the addition of chondroitin sulfate. Among them, the specimen prepared by compounding chondroitin sulfate into calcium from sea urchin shells indicated a high calcium absorption ratio. Furthermore, a somewhat high absorption ratio of calcium is observed even in the composition of calcium lactate from sea urchin shells to which no chondroitin sulfate was added, suggesting that sea urchin shell itself is a calcium source excellent in the absorbability. Further, in the Composition obtained by substituting lactic acid in Example 1 for succinic acid showed almost the same absorption ratio of calcium as in the composition containing UCAL*. On the other hand, in the composition of calcium carbonate obtained by treating eggshells in a conventional manner, the absorption ratio of calcium was about ⅕ of that in the composition containing UCAL*.

Experimental Example 2

Figure 2:
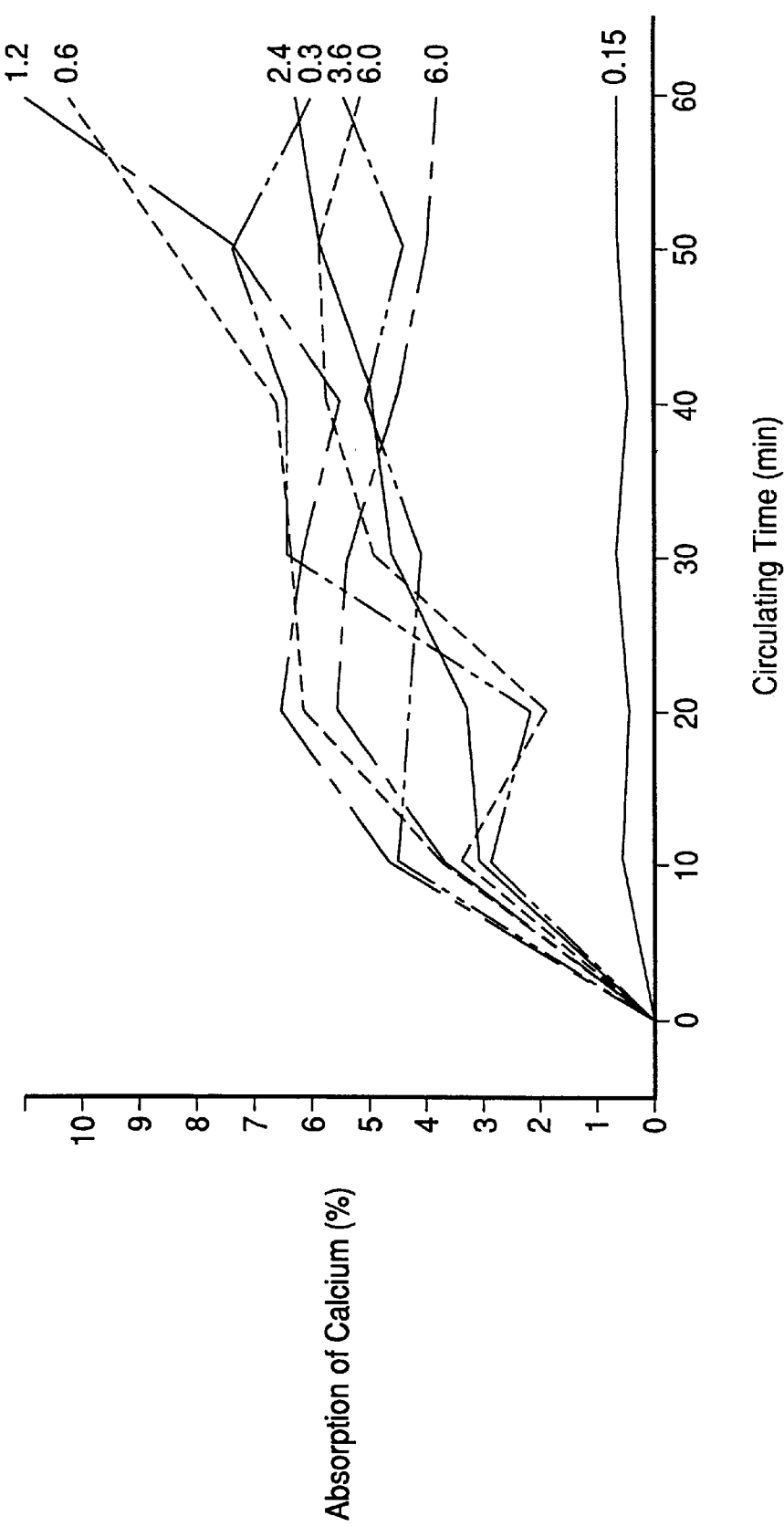
FIG. 2 is a graph which illustrates the absorption of calcium (%) into rat's intestines with time (min), in a case of administrating calcium lactate originating in sea urchin shells obtained in Example 1 while varying the concentration of chondroitin sulfate within a range of 0.15 to 6% by weight.

Change of Absorption Ratio of Calcium with Addition Amount of Chondroitin Sulfate Test for the absorption of calcium was carried out in the same manner as in Experimental Example 1 using compositions containing the compound UCAL* tested in Example 1, in which the ratio of chondroitin sulfate (100%) was changed to six levels of concentration from 0.6 to 6% by weight on the basis of calcium (ratio of the composition containing 20% chondroitin sulfate to calcium lactate : 0.5 to 5% by weight). Furthermore, in order to confirm the lower limit for the amount of chondroitin sulfate to be added, experiment was carried out in the same manner as above with the ratio of chondroitin sulfate to calcium being set at 0.15% and 0.3% by weight respectively. The results are shown in Table 2 and FIG. 2. In the graph of FIG. 2, the ordinate indicates the absorption ratio of calcium (%) and the abscissa indicates the circulating time (min).

TABLE 2

| Chondroitin Sulfate/Ca conc. (%) | Circulating time (min) | | | | | |
|---|---|---|---|---|---|---|
| | 10 | 20 | 30 | 40 | 50 | 60 |
| 0.15 | 0.60 ± 0.54 | 0.49 ± 0.44 | 0.70 ± 0.55 | 0.50 ± 0.29 | 0.65 ± 0.22 | 0.64 ± 0.28 |
| 0.3 | 2.96 ± 0.89 | 2.22 ± 0.83 | 6.42 ± 2.00 | 6.44 ± 2.27 | 7.29 ± 2.31 | 5.92 ± 1.92 |
| 0.6 | 3.78 ± 0.06 | 6.15 ± 0.17 | 6.32 ± 0.10 | 6.56 ± 0.05 | 8.36 ± 0.10 | 10.16 ± 0.20 |
| 1.2 | 4.68 ± 0.64 | 6.54 ÷ 0.64 | 6.13 ± 0.38 | 5.49 ± 0.62 | 7.15 ± 0.40 | 10.93 ± 0.33 |
| 2.4 | 3.14 ± 0.19 | 3.32 ± 0.12 | 4.62 ± 0.10 | 4.88 + 0.16 | 5.79 ± 0.10 | 6.20 ± 0.14 |
| 3.6 | 4.56 ± 0.23 | 4.31 ± 0.50 | 4.12 ± 0.28 | 5.05 ± 0.34 | 4.39 ± 0.23 | 4.88 ± 0.09 |
| 4.8 | 3.46 ± 0.04 | 1.94 ± 0.03 | 4.97 ± 0.36 | 5.72 ± 0.14 | 5.83 ± 0.08 | 5.10 ± 0.07 |
| 6.0 | 3.73 ± 0.13 | 5.57 ± 0.17 | 5.37 ± 0.17 | 4.52 ± 0.06 | 3.98 ± 0.02 | 3.78 ± 0.26 |

As is apparent from the above results, the absorption ratio of calcium is high when the proportion of chondroitin sulfate to calcium is in a range of 0.2 to 5.0% by weight, particulaly, 0.3 to 2.5% by weight, the absorption ratio gradually decreases as the concentration of chondroitin sulfate increases from 2 to 5% by weight, and when the concentration reaches 5% by weight, the value decreases to about one-half compared with the case of 1% which is the concentration giving the maximum absorption. On the other hand, chondroitin sulfate shows satisfactory Ca absorption ratio even around 0.3% by weight, but the value is rapidly lowered at 0.15% by weight and t is considered that the practical lower limit of the concentration of chondroitin sulfate to calcium is about 0.2% by weight.

In Experimental Example 1 and Experimental Example 2 regarding the absorption ratio of calcium for each of the foregoing types, little difference was observed in calcium concentration in plasmas obtained from blood sampling taken before and after perfusion, among the groups and before and after perfusion, whatever value the concentration of chondroitin sulfate may be, and it was within the normal range of a living body.

Experimental Example 3
Rat $LD_{50}$ Test for Calcium from Sea Urchin Shells

Acute toxicity of calcium from sea urchin shells, which were used as one of starting materials for the compositions in the examples of the present invention, was determined by a Rat $LD_{50}$ Test.

0.5% solution of calcium, $Ca(OH)_2$ from sea urchin shells was adjusted to pH 5.0 with 50% L-lactic acid (U-grade), administrated orally (1000 to 5000 mg/kg) and intravenously (100 to 290 mg/kg) to rats (SD male) of 7 week-old (200 g in body weight) and observation was made for 14 days to obtain $LD_{50}$ values.

During the observation period in the oral administration, for the groups administrate with each of doses (50 rats in total), since only 3 deaths were identified in a case of giving actually administratable dose of 5000 mg/kg and no death was identified for other groups, $LD_{50}$ value could not be calculated, so that the $LD_{50}$ value was assumed primafacie as 5000 mg/kg. On the other hand, in a case of groups for intravenous administration, the $LD_{50}$ value was 187.0 mg/kg. From the results described above, it can be considered that the compositions which contain calcium from sea urchin shells according to the present invention are extremely safe when used as calcium preparations or food additives.

INDUSTRIAL AVAILABILITY

As described above, a composition containing readily absorbable calcium with addition of chondrontin sulfate according to the present invention markedly promotes the absorption of calcium in vivo. In particular, when using sea urchin shells which are fishery wastes and considered to be of little utility value at present as the raw material, calcium originating in sea urchin shells which exhibits an excellent absorbability in vivo can be obtained, and a composition obtained by compounding the same has an application use as calcium preparations, as well as a variety of foods and food additives excellent in taste and flavor.

I claim:

1. A calcium-containing composition for use in food comprising a calcium salt and 0.2 to 2.5% by weight, on the basis of the calcium content, of chondroitin sulfate for making calcium readily absorbable.

2. A calcium-containing composition as defined in claim 1, wherein the calcium salt is a salt of an organic carboxylic acid selected from the group consisting of L-Lactic acid, citric acid, malic acid, succinic acid, gluconic acid, L-ascorbic acid and acetic acid.

3. A calcium-containing composition as defined in claim 1, wherein the calcium salt is a calcium carbonate.

4. A calcium-containing composition as defined in claim 1, wherein a calcium salt is a salt of an organic carboxylic acid and obtained by treating external skeletons of sea urchins.

5. A process for producing a calcium-containing composition, wherein the process comprises baking and hydrating external skeletons of sea urchins thereby forming calcium hydroxide, which is then neutralized by reaction with an organic carboxylic acid, and adding 0.2 to 2.5% by weight,on the basis of a calcium content, of chondroitin sulfate.

* * * * *